(12) United States Patent
Mishima et al.

(10) Patent No.: US 9,033,004 B2
(45) Date of Patent: May 19, 2015

(54) GUIDE WIRE

(75) Inventors: Katsuro Mishima, Yugawara-machi (JP); Yutaka Itou, Fujinomiya (JP); Hiraku Murayama, Fuji (JP); Hideo Satou, Fujinomiya (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 13/477,616

(22) Filed: May 22, 2012

(65) Prior Publication Data

US 2012/0228273 A1    Sep. 13, 2012

Related U.S. Application Data

(62) Division of application No. 12/842,458, filed on Jul. 23, 2010, now Pat. No. 8,313,445, which is a division of application No. 11/013,384, filed on Dec. 17, 2004, now Pat. No. 7,785,274.

(30) Foreign Application Priority Data

Dec. 18, 2003 (JP) ................... 2003-421659
Jan. 19, 2004 (JP) ................... 2004-011185
Jan. 30, 2004 (JP) ................... 2004-024573

(51) Int. Cl.
*B21F 15/02* (2006.01)
*A61B 5/00* (2006.01)
*A61M 25/09* (2006.01)

(52) U.S. Cl.
CPC ..... *A61M 25/09* (2013.01); *A61M 2025/09091* (2013.01); *A61M 2025/09133* (2013.01); *A61M 2025/0915* (2013.01)

(58) Field of Classification Search
CPC .......... A61M 2025/09108; A61M 2025/09133

USPC .......................................... 600/585
See application file for complete search history.

(56) References Cited

U.S. PATENT DOCUMENTS 3,522,644 A * 8/1970 Cavagnero ............... 29/898.066
4,925,445 A   5/1990 Sakamoto et al.
(Continued)

FOREIGN PATENT DOCUMENTS

DE    196 07 595 A1    9/1997
EP    0 473 790 A1    3/1992
(Continued)

OTHER PUBLICATIONS

JP2003-159333.*

*Primary Examiner* — Brian Szmal
*Assistant Examiner* — H. Q. Nguyen
(74) *Attorney, Agent, or Firm* — Buchanan, Ingersoll & Rooney PC (57) ABSTRACT

A guide wire includes a wire body having a first wire disposed at a distal end and a second wire joined to a proximal end of the first wire at a joint by welding. The joint is curved. In the joint, at least one component (e.g., Ti) of the material of the first wire decreases toward the proximal end and at least one component (e.g., Fe) of the material of the second wire decreases toward the distal end. When a tensile test is conducted on a region of the wire body including the joint, the region of the wire body has, in a tensile load and elongation diagram, an elastic section extending substantially straight upwardly to the right, a yield section extending substantially horizontally or upwardly to the right from the elastic section, and a substantially straight section extending upwardly to the right from the yield section.

10 Claims, 8 Drawing Sheets

(56) References Cited

U.S. PATENT DOCUMENTS

| | | | |
|---|---|---|---|
| 5,069,226 A | 12/1991 | Yamauchi et al. | |
| 5,111,829 A | 5/1992 | Alvarez de Toledo | |
| 5,152,855 A * | 10/1992 | Jansman et al. | 156/73.5 |
| 5,171,383 A | 12/1992 | Sagae et al. | |
| 5,341,818 A | 8/1994 | Abrams et al. | |
| 5,358,796 A | 10/1994 | Nakamura et al. | |
| 5,365,943 A | 11/1994 | Jansen | |
| 5,368,661 A | 11/1994 | Nakamura et al. | |
| 5,411,476 A | 5/1995 | Abrams et al. | |
| 5,431,506 A | 7/1995 | Masunaga | |
| 5,636,641 A | 6/1997 | Fariabi | |
| 5,670,071 A * | 9/1997 | Ueyama et al. | 219/130.51 |
| 5,720,300 A | 2/1998 | Fagan et al. | |
| 5,769,796 A | 6/1998 | Palermo et al. | |
| 6,001,068 A | 12/1999 | Uchino et al. | |
| 6,488,637 B1 | 12/2002 | Eder et al. | |
| 6,508,803 B1 | 1/2003 | Horikawa et al. | |
| 6,592,570 B2 | 7/2003 | Abrams et al. | |
| 6,602,228 B2 | 8/2003 | Nanis et al. | |
| 6,702,762 B2 | 3/2004 | Jafari et al. | |
| 2003/0069521 A1 | 4/2003 | Reynolds et al. | |
| 2003/0125641 A1 | 7/2003 | Jafari et al. | |
| 2004/0030265 A1 | 2/2004 | Murayama et al. | |
| 2004/0030266 A1 | 2/2004 | Murayama et al. | |
| 2004/0039308 A1 | 2/2004 | Murayama et al. | |
| 2004/0039309 A1 | 2/2004 | Murayama et al. | |
| 2006/0047223 A1 | 3/2006 | Grandfield et al. | |

FOREIGN PATENT DOCUMENTS

| | | |
|---|---|---|
| EP | 0 806 220 A2 | 12/1997 |
| EP | 0 838 230 A2 | 4/1998 |
| JP | 1-124473 A | 5/1989 |
| JP | 7-068386 A | 3/1995 |
| JP | 9-038210 A | 2/1997 |
| JP | 2001-205449 A | 7/2001 |
| WO | WO 96/25969 A2 | 8/1996 |

* cited by examiner

GUIDE WIRE

This application is a divisional of application Ser. No. 12/842,458, filed on Jul. 23, 2010, which is a divisional of application Ser. No. 11/013,384, filed on Dec. 17, 2004, which is based on and claims priority under 35 U.S.C. §119 with respect to Japanese Application Nos. 2003-421659 filed on Dec. 18, 2003, 2004-011185 filed on Jan. 19, 2004 and 2004-024573 filed on Jan. 30, 2004. The entire content of the prior applications is incorporated herein by reference.

FIELD OF THE INVENTION

The present invention generally relates to a guide wire, and more particularly pertains to a guide wire for use in introducing a catheter into a body cavity such as a blood vessel.

BACKGROUND DISCUSSION

Guide wires are used to guide a catheter for treating a body region at which a surgical operation such as PTCA (Percutaneous Transluminal Coronary Angioplasty) cannot be performed. Guide wires are also used to guide a catheter for treating a human body on a minimally invasive basis, or diagnosing a cardiovascular according to angiography. A guide wire used in PTCA is combined with a balloon catheter such that the distal end of the guide wire projects from the distal end of the balloon catheter, and is inserted together with the balloon catheter into a position near a constricted area of a blood vessel. Then, the guide wire guides the distal end of the balloon catheter to the stenosis area of the blood vessel.

Blood vessels oftentimes possess an intricately curved shape. Guide wires used to insert balloon catheters into such blood vessels are required to have flexibility and elasticity upon bending, pushability and torque transmission performance for transmitting a control action on the proximal end toward the distal end (these features will be collectively referred to as "steerability"), and kink resistance (fold resistance). Guide wire structures for achieving flexibility among the above features include a structure in which a metal coil having flexibility upon bending is wound around a core at the slender distal end of a guide wire and a structure in which a superelastic wire of Ni—Ti or the like is used as a guide wire core for giving flexibility and elasticity.

Conventional guide wires have a core made essentially of one material. For increased steerability of guide wires, the core is made of a material having a relatively high modulus of elasticity, which tends to make the distal end of the guide wire less flexible. If the core is made of a material having a relatively low modulus of elasticity for making the distal end of the guide wire more flexible, then the proximal end of the guide wire loses its steerability. It has been difficult to achieve both flexibility and steerability with one core material.

SUMMARY

The guide wire described here comprises a wire body having a first wire disposed at a distal end thereof and a second wire joined to the proximal end of the first wire by way of a joint, with the second wire being made of a material having an elastic constant greater than the material of the first wire. In addition, the joint between the first wire and the second wire has a curved shape which is symmetric with respect to the central axis of the wire body.

The joint is preferably convex toward the proximal end of the wire body, and the first and second wires are preferably joined to each other by welding. The joint preferably includes or is in the form of a layer. The joint in the form of a layer preferably has a thickness ranging from 0.001 µm to 100 µm. The wire body preferably has an outside diameter at the joint which is greater than the outside diameter of a region of the wire body on a proximal side of the joint. The wire body preferably has an outside diameter at the joint which is greater than the outside diameters of regions of the wire body on proximal and distal sides of the joint. The guide wire preferably has a covering layer disposed on an outer circumferential surface of the wire body in covering relation to at least the joint. The covering layer is preferably made of a material capable of reducing friction, such as thermoplastic elastomer, silicone resin, or fluorine-based resin. The covering layer preferably has an average thickness in the range from 1 µm to 30 µm. The wire body preferably has a tapered portion whose outside diameter is progressively reduced toward the distal end. The guide wire preferably has a helical coil disposed around at least a distal end portion of the first wire. Preferably, the materials of the first wire and the second wire contain a common metal element. The first wire is preferably made of a superelastic alloy, while the second wire is preferably made of stainless steel or a Co base alloy. The Co base alloy is preferably a Co—Ni—Cr base alloy.

According to another aspect, the guide wire described here comprises a wire body having a first wire disposed at a distal end thereof and a second wire joined to a proximal end of the first wire through a joint, with the second wire being made of a material different from the material of the first wire. In the joint, a first component of the material of the first wire decreases toward the proximal end and a second component of the material of the second wire decreases toward the distal end.

The material of the second wire preferably has an elastic constant greater than the material of the first wire. The materials of the first wire and the second wire preferably contain a common metal element. The first wire is preferably made of an Ni—Ti base alloy, while the second wire is preferably made of stainless steel or a Co base alloy. The Co base alloy is preferably a Co—Ni—Cr base alloy. The joint is preferably of a curved shape, and of a shape which is symmetrical with respect to the central axis of the wire body. The joint is preferably convex toward the proximal end of the wire body, and the first and second wires are preferably joined to each other by welding. The joint in the form of a layer preferably has a thickness ranging from 0.001 µm to 100 µm. The wire body preferably has an outside diameter at the joint which is greater than the outside diameters of regions of the wire body on proximal and distal sides of the joint. The guide wire preferably has a covering layer disposed on an outer circumferential surface of the wire body in covering relation to at least the joint. The covering layer is preferably made of a material capable of reducing friction, such as thermoplastic elastomer, silicone resin, or fluorine-based resin. The covering layer preferably has an average thickness in the range from 1 µm to 30 µm. The wire body preferably has a tapered portion whose outside diameter is progressively reduced toward the distal end. The guide wire preferably has a helical coil disposed around at least a distal end portion of the first wire. In the joint, the first component and/or the second component preferably has a plurality of different concentration gradients in the longitudinal direction of the wire body. The different concentration gradients include a first concentration gradient and a second concentration gradient which are relatively gradual, and a third concentration gradient positioned between the first concentration gradient and the second concentration gradient and steeper than the first concentration gradient and the second concentration gradient.

In accordance with another aspect, the guide wire described here comprises a wire body having a first wire disposed at a distal end thereof and made of a pseudoelastic material, and a second wire joined to a proximal end of the first wire by way of a joint produced by welding. The second wire is made of a material having an elastic constant greater than that of the material of the first wire. A region of the wire body including the joint has, in a tensile load and elongation diagram, an elastic section extending substantially straight upwardly to the right and a yield section extending substantially horizontally or upwardly to the right from the elastic section, with such region of the wire body having characteristics such that upon tensile loading the region is fracturable at a fracture position under a load higher than a terminal end of the yield section. The fracture position is located other than on or at the joint.

According to another aspect, the guide wire described here comprises a wire body having a first wire disposed at a distal end thereof and made of a pseudoelastic material, and a second wire joined to a proximal end of the first wire through a joint by welding and made of a material having an elastic constant greater than that of the material of the first wire. When a tensile test is conducted on a region of the wire body including the joint, the region of the wire body has, in a tensile load and elongation diagram, an elastic section extending substantially straight upwardly to the right, a yield section extending substantially horizontally or upwardly to the right from the elastic section, and a substantially straight section extending upwardly to the right from the yield section, with such region of the wire body having characteristics such that the region is fracturable near a terminal end of the straight section, with the joint possessing a higher fracture strength than the distal end of the second wire.

In accordance with a further aspect, the disclosed guide wire comprises a wire body having a first wire disposed at a distal end thereof and made of a pseudoelastic material, a second wire made of a material having an elastic constant greater than that of the material of the first wire, and a joint produced by joining a proximal end of the first wire and a distal end of the second wire to each other by welding. The joint possesses a higher fracture strength than the distal end of the second wire.

In a tensile load and elongation diagram, the diagram preferably includes a tensile load and elongation curve which is curved downwardly due to necking of the guide wire when the guide wire is going to be fractured. The wire body preferably has a fracture strength of at least 4 kgf. The first wire is preferably made of a superelastic alloy, while the second wire is preferably made of stainless steel or a Co base alloy. The joint between the first wire and the second wire is preferably of a curved shape which is symmetric with respect to the central axis of the wire body. The joint is preferably convex toward the proximal end of the wire body and preferably includes or is in the form of a layer. The joint in the form of a layer preferably has a thickness ranging from 0.001 µm to 100 µm. A covering layer applied to at least a portion of the wire body is preferably made of a material capable of reducing friction, such as thermoplastic elastomer, silicone resin, or fluorine-based resin. The covering layer preferably has an average thickness in the range from 1 µm to 30 µm. The wire body preferably has a tapered portion whose outside diameter is progressively reduced toward the distal end. The guide wire can also have a helical coil disposed around at least a distal end portion of the first wire. Preferably, the materials of the first wire and the second wire contain a common metal element.

According to a further aspect, the guide wire described here comprises a wire body having a first wire disposed at a distal end thereof and a second wire joined to the proximal end of the first wire through a weld joint and made of a material different from the material of the first wire. The materials of the first wire and the second wire contain a common metal element, with the first wire made of a Ni—Ti base alloy. The weld joint includes at least one portion in which at least one component of the material of the first wire decreases toward the proximal end, and at least another portion in which the at least one component of the material of the second wire decreases toward the distal end.

The disclosed guide wire according to another aspect comprises a wire body having a first wire disposed at a distal end thereof and a second wire joined to the proximal end of the first wire through a weld joint and made of a material different from the material of the first wire, with the materials of the first wire and the second wire containing a common metal element. The first wire is made of a Ni—Ti base alloy, and the weld joint includes at least one portion such that at least one component of the material of the first wire decreases toward the proximal end.

The disclosed guide wire in accordance with another aspect comprises a wire body having a first wire disposed at a distal end thereof and a second wire joined to the proximal end of the first wire through a weld joint and made of a material different from the material of the first wire, with the materials of the first wire and the second wire containing a common metal element. The first wire is made of a Ni—Ti base alloy, and the weld joint includes at least one portion such that at least one component of the material of the second wire decreases toward the distal end.

The above and other features and characteristics of the disclosed guide wire will become more apparent from the following detailed description considered together with the accompanying drawing figures which illustrate by way of example on embodiment of the guide wire.

BRIEF DESCRIPTION OF THE DRAWING FIGURES

FIGS. 5(*a*) and 5(*b*) are diagrams each showing the relationship between tensile loads and elongations in tensile tests conducted on the wire body shown in FIG. 1.

DETAILED DESCRIPTION

Figure 1:
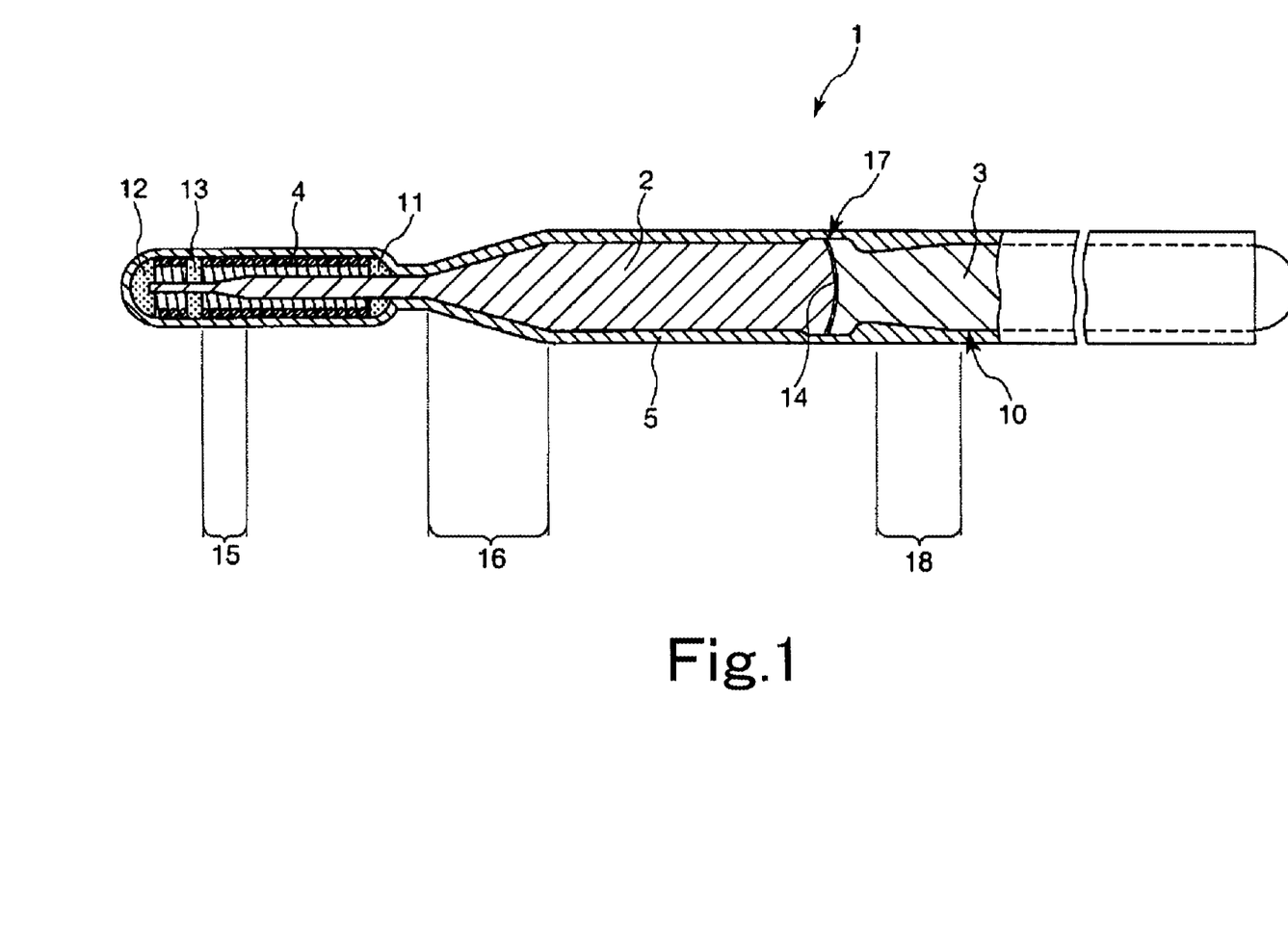
FIG. 1 is a longitudinal cross-sectional view of a guide wire according to an embodiment of the present invention.

Referring initially to FIG. 1, a guide wire according to one embodiment is illustrated as being contracted in the longitudinal direction and as being enlarged or exaggerated in the transverse direction for an easier understanding of the invention. Therefore, the ratio of the illustrated dimensions in the longitudinal and transverse directions is different from the ratio of the actual dimensions.

The guide wire 1 is a guide wire to be inserted in a catheter and includes a wire body 10 having a first wire 2 disposed at a distal end thereof and a second wire 3 disposed at a proximal end thereof and joined to the first wire 2, and a helical coil 4 combined with the wire body 10. The guide wire 1 has an overall length which is preferably in the range from 200 mm to 5,000 mm. The guide wire 1 has an outside diameter, i.e., an outside diameter over a constant-outside-diameter portion thereof, which is preferably in the range from 0.2 mm to 1.4 mm.

The first wire 2 is made of an elastic wire material and has a length which is preferably in the range from 20 mm to 1,000 mm.

According to this disclosed embodiment, a portion of the first wire 2 possesses a constant outside diameter and another portion (tapered portion) possesses an outside diameter progressively smaller toward the distal end. The first wire 2 may have one or two or more tapered portions. In the illustrated embodiment, the first wire 2 possesses two tapered portions 15, 16.

The first wire 2 with the two tapered portions 15, 16 possesses rigidities (flexural rigidity and torsional rigidity) that are gradually reduced toward the distal end. As a result, the guide wire 1 is flexible enough at the distal end portion for a higher ability to follow curved blood vessels, better safety, and greater resistance to forces tending to kink the guide wire 1.

In the illustrated embodiment, the tapered portions 15, 16 are disposed in longitudinally spaced apart locations on the first wire 2. However, the first wire 2 may be tapered in its entirety toward the distal end. The tapered portions 15, 16 may be tapered at an angle (diameter reduction ratio) which is constant in the longitudinal direction or at angles (diameter reduction ratios) which are different in the longitudinal direction. For example, the tapered portions 15, 16 may be tapered at an alternating pattern of relatively large angles (diameter reduction ratios) and relatively small angles (diameter reduction ratios).

It is also to be noted that the configuration shown in FIG. 1 can be varied in that the tapered portion 16 may have a proximal end positioned somewhere on the second wire 3, e.g., the tapered portion 16 may be positioned across a joined (welded) area 14 between the first wire 2 and the second wire 3.

The first wire 2 may be made of any material, e.g., any of various metal materials such as stainless steel. Particularly, the first wire 2 is preferably made of a pseudoelastic alloy (including a superelastic alloy), and more preferably is made of a superelastic alloy. Superelastic alloys are relatively flexible, elastic, and less plastically deformable. Therefore, if the first wire 2 is made of a superelastic alloy, the guide wire 1 is sufficiently flexible and elastic upon bending at its distal end portion, and has a better ability to follow blood vessels that are curved and bent intricately so that the guide wire 1 has higher steerability. In addition, even when the second wire 2 is repeatedly curved or bent, since the first wire 2 is less plastically deformable due to its elasticity, any reduction in the steerability of the guide wire 1 which would otherwise be caused if the first wire 2 were more plastically deformable, is generally avoided.

Pseudoelastic alloys include all pseudoelastic alloys which exhibit any tensile stress and strain curves, all pseudoelastic alloys which have transformation temperatures such as As, Af, Ms, Mf, etc. that can or cannot be measured distinctly, and all pseudoelastic alloys which are greatly deformed (strained) under stresses and recover the original shape upon removal of the stresses.

Preferred compositions of superelastic alloys include an Ni—Ti base alloy such as an Ni—Ti alloy having 49 to 52 at % of Ni, a Cu—Zn alloy having 38.5 to 41.5 wt % of Zn, a Cu—Zn—X alloy (X represents at least one of Be, Si, Sn, Al, and Ga) having 1 to 10 wt % of X, and an Ni—Al alloy having 36 to 38 at %. A particularly preferable alloy of those mentioned is the Ni—Ti base alloy. The superelastic alloys typified by the Ni—Ti base alloy are excellent in its adhesion to a covering layer 5 to be described later.

The second wire 3 has a distal end connected (joined) to the proximal end of the first wire 2 by, for example, welding so that the two wires 2, 3 are fixed to one another. The second wire 3 is preferably made of an elastic wire material and has a length which is preferably in the range from 20 mm to 4,800 mm.

The second wire 3 is preferably made of a material having elastic constants (Young's modulus (tensile modulus), modulus of rigidity (shear modulus), and bulk modulus) which are different from the first wire 2. Particularly, the second wire 3 is preferably made of a material having elastic constants which are greater than the first wire 2. The second wire 3 made of such a material has appropriate rigidities (flexural rigidity and torsional rigidity), and imparts rigidity to the guide wire 1 for increased pushability and torque transmission capability to give excellent insertion steerability.

The second wire 3 can be made of any materials. For example, the second wire 3 may be made of any of various metal materials including stainless steels (all types of SUS, e.g., SUS304, SUS303, SUS316, SUS316L, SUS316J1, SUS316J1L, SUS405, SUS430, SUS434, SUS444, SUS429, SUS430F, SUS302, etc.), piano wire, cobalt base alloys, and pseudoelastic alloys. The second wire 3 may be made of intermetallic materials.

Of these metal materials, the cobalt base alloys have high elastic constants and appropriate elastic limits when processed into wires. Therefore, the second wire 3 made of a cobalt base alloy has a particularly excellent torque transmission capability and is highly unlikely to give rise to problems such as buckling. Any cobalt base alloys containing Co as a constituent element may be employed. However, cobalt base alloys containing Co as a chief component (cobalt base alloys wherein the content of Co has a largest wt % among the elements making up the alloys) are preferable, and Co—Ni—Cr base alloys are more preferable. The second wire 3 made of any of alloys of the above compositions make the above advantages more significant. Since the alloys of the above compositions have plasticity when deformed at the normal temperature, they can easily be deformed into desired shapes when in use. The alloys of the above compositions have high elastic constants and can be cold-formed with high elastic limits into a small-diameter wire while sufficiently preventing buckling on account of high elastic limits, with the wire having sufficient elasticity and rigidity for insertion into desired body regions.

Preferable Co—Ni—Cr base alloys include alloys containing 28 to 50 wt % of Co, 10 to 30 wt % of Ni, 10 to 30 wt % of Cr, and the balance being Fe and inevitable impurities, and similar alloys having one of the elements replaced with another element (substitute element). An alloy containing a substitute element exhibits an advantage inherent in the substitute element. For example, if the second wire 3 contains at least one selected from Ti, Nb, Ta, Be, and Mo as a substitute element, the mechanical strength of the second wire 3 can be increased. If the second wire 3 contains elements (substitute elements) other than Co, Ni, Cr, the total content of those substitute elements is preferably 30 wt % or less.

Part of the Co, Ni, Cr may be replaced with another element or elements. For example, part of the Ni may be replaced with Mn for better workability. Part of the Cr may be replaced with Mo and/or W for a higher elastic limit. Of the Co—Ni—Cr base alloys, Co—Ni—Cr—Mo base alloys containing Mo are particularly preferable.

Specific compositions of the Co—Ni—Cr base alloys include (1) 40 wt % of Co, 22 wt % of Ni, 25 wt % of Cr, 2 wt % of Mn, 0.17 wt % of C, 0.03 wt % of Be, and Fe(balance), (2) 40 wt % of Co, 15 wt % of Ni, 20 wt % of Cr, 2 wt % of Mn, 7 wt % of Mo, 0.15 wt % of C, 0.03 wt % of Be, and Fe(balance), (3) 42 wt % of Co, 13 wt % of Ni, 20 wt % of Cr, 1.6 wt % of Mn, 2 wt % of Mo, 2.8 wt % of W, 0.2 wt % of C, 0.04 wt % of Be, and Fe(balance), (4) 45 wt % of Co, 21 wt % of Ni, 18 wt % of Cr, 1 wt % of Mn, 4 wt % of Mo, 1 wt % of Ti, 0.02 wt % of C, 0.3 wt % of Be, and Fe(balance), (5) 34 wt % of Co, 21 wt % of Ni, 14 wt % of Cr, 0.5 wt % of Mn, 6 wt % of Mo, 2.5 wt % of Nb, 0.5 wt % of Ta, and Fe(balance). The Co—Ni—Cr base alloys referred to in the present invention include these alloys.

If the second wire 3 is made of stainless steel, the guide wire 1 has better pushability and torque transmission capability.

The first wire 2 and the second wire 3 are preferably made of different alloys. The first wire 2 is preferably made of a material having elastic constants smaller than the second wire 3. With these materials, the guide wire 1 has a distal end portion of excellent flexibility and a proximal end of high rigidities (flexural rigidity and torsional rigidity). As a result, the guide wire 1 has excellent pushability and torque transmission capability for better steerability, and the distal end portion thereof gains better flexibility and elasticity for increased ability to follow blood vessels and for increased safety.

According to one specific combination of the first wire 2 and the second wire 3, the first wire 2 is preferably made of a superelastic alloy (particularly an Ni—Ti base alloy) and the second wire 3 is preferably made of a Co base alloy (particularly, a Co—Ni—Cr base alloy) or stainless steel (an Fe—Cr—Ni base alloy) for making the above advantages more significant. Another reason for which the above combination is preferable is that the materials of the first wire 2 and the second wire 3 contain a common metal element (e.g., Ni). When the first wire 2 and the second wire 3 are welded to each other as mentioned above and described later, the bonding strength of the joint 14 is increased by the common metal element. When the guide wire 1 thus constructed is inspected in a tensile test as described later, the joint 14 is prevented from fracture. The guide wire 1 will thus be highly reliable and safe in actual use in living bodies.

In the illustrated embodiment, the second wire 3 has a generally constant outside diameter, and includes a tapered portion 18 near its distal end, i.e., near the joint 14, with the tapered portion 18 possessing an outside diameter which becomes progressively smaller toward the distal end of the second wire. The tapered portion 18 causes the physical properties, especially the elasticity, from the second wire 3 to the first wire 2 to change relatively smoothly, providing excellent pushability and torque transmission performance across the joint 14 and increased kink resistance. Alternatively, the second wire 3 may include a portion having lower yield stresses or elastic constants than the other portion thereof near the distal end of the second wire 3. The distal end portion of the second wire 3 is thus more flexible than the other portion of the second wire. The first wire 2 is more flexible than the distal end portion of the second wire 3. The guide wire 1 which is thus made more flexible stepwise toward the distal end thereof has excellent pushability, torque transmission performance, and kink resistance.

The coil 4 includes a helically coiled filament (thin filament) and is disposed around the distal end portion of the first wire 2. In the illustrated embodiment, the distal end portion of the first wire 2 extends substantially centrally through the coil 4 out of contact with the inner surface of the coil 4. The joined boundary area 14 is positioned more closely to the proximal end of the guide wire 1 than the proximal end of the coil 4.

In the illustrated embodiment, the coil 4 has helically wound turns that are spaced apart in the absence of external forces applied thereto. However, the coil 4 may have helically wound turns that are held in close contact in the absence of external forces applied thereto.

The coil 4 is preferably made of a metal material such as stainless steel, superelastic alloy, cobalt base alloy, precious metal such as gold, platinum, tungsten, or the like, or alloy containing precious metals, e.g., platinum-iridium alloy. If the coil 4 is made of an X-ray impermeable material such as precious metal, the guide wire 1 is made radiopaque, and hence can be inserted into a living body while the distal end thereof is being positionally confirmed according to radioscopy. The coil 4 may be made of different materials respectively at the distal and proximal end portions thereof. For example, the distal end portion of the coil 4 may be made of an X-ray impermeable material and the proximal end portion of the coil 4 may be made of a relatively X-ray permeable material such as stainless steel. The overall length of the coil 4 is preferably in the range from 5 mm to 500 mm.

The distal and proximal ends of the coil 4 are fixed to the first wire 2 by respective fixing materials 11, 12. The coil 4 also has an intermediate portion (closer to the distal end) fixed to the first wire 2 by a fixing material 13. The fixing materials 11, 12, 13 include a solder material (brazing material). Alternatively, the fixing materials 11, 12 and 13 may include an adhesive. The coil 4 may be fixed in place by welding, rather than the fixing materials. The fixing material 12 preferably has a round distal end surface for preventing blood vessel walls from being damaged.

According to the illustrated embodiment, since the first wire 2 which is partly covered with the coil 4 has a relatively small area of contact with a blood vessel wall, the guide wire 1 undergoes reduced resistance to its sliding movement, and hence has better steerability.

According to the illustrated embodiment, the filament of the coil 4 has a circular cross-sectional shape. However, the filament of the coil 4 may have an elliptical cross-sectional shape, a square cross-sectional shape (particularly an elongate rectangular cross-sectional shape), or the like.

The first wire 2 and the second wire 3 that construct the guide wire 10 are preferably connected to each other by welding. The joint (welded area) 14 of the first wire 2 and the second wire 3 that are thus connected to each other has such a high bonding strength that torsional torques and pushing forces can be reliably transmitted from the second wire 3 to the first wire 2.

Figure 2:
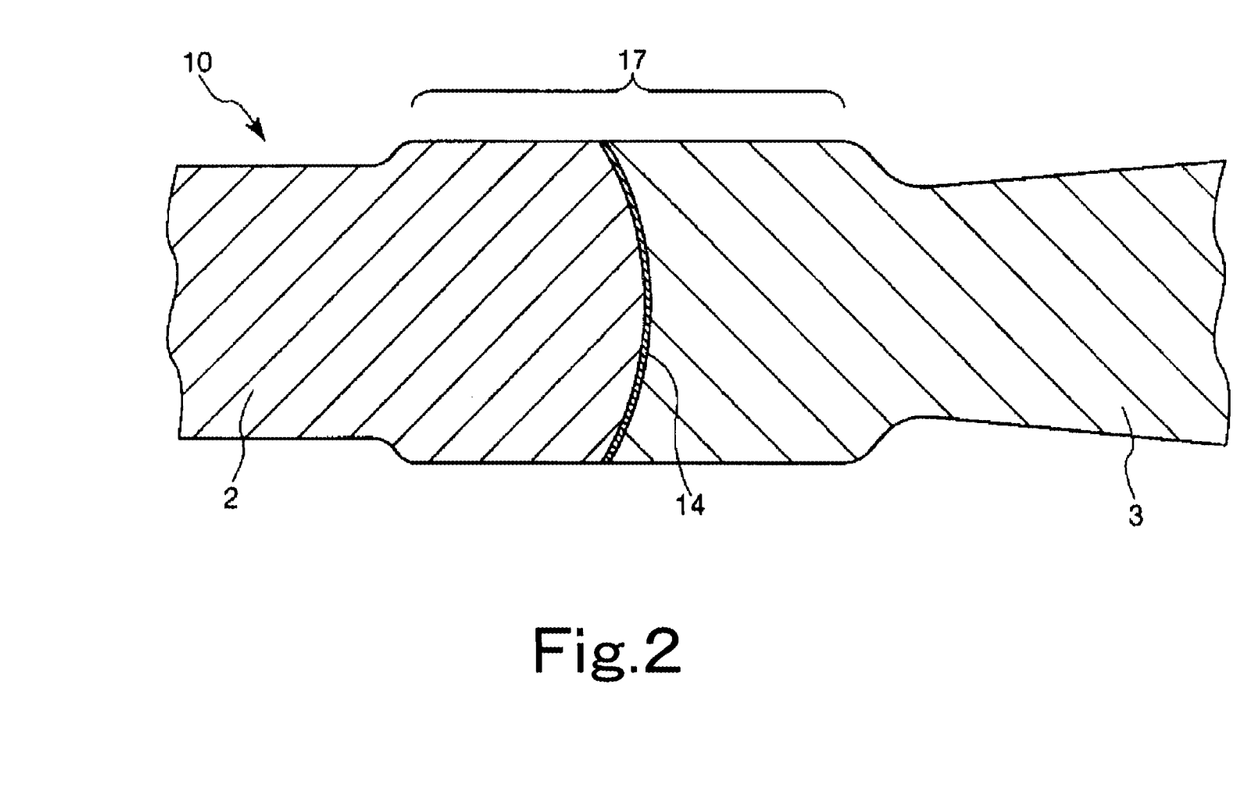
FIG. 2 is an enlarged longitudinal cross-sectional view of a joined region of a wire body of the guide wire shown in FIG. 1.

As shown in FIG. 2, the joint 14 is in the form of a layer. The term "layer" used herein covers not only a visually perceptible layer, but also a conceptual layer such as a distinctive content change, for example. The laminar joint 14 extends in a direction substantially perpendicular to the axis of the wire body 10. The joint 14 may be convex. The laminar joint 14 is preferably convex toward the axis of the wire body 10. Particularly, the joint 14 may be convex toward the proximal end of the wire body 10 as shown in FIG. 1. Alternatively, the joint 14 may be convex toward the distal end of the wire body 10. The joint 14 may be configured to be convex toward one of the wires formed of a material having an elastic constant greater than the material of the other wire. Alternatively, the joint 14 may be convex toward one of the wires formed of a material having an elastic constant lower than the material of the other wire. The curved shape of the joint 14 is preferably substantially symmetric with respect to the central axis of the wire body 10. Specifically, the curved shape of the joint 14 is preferably shaped as a body of rotation about the central axis of the wire body 10. The body of rotation may be of a dish shape, a spherical shape, a parabolic shape, or a shape similar to one of those shapes. The thickness of the laminar joint 14 is preferably in the range from 0.001 µm to 100 µm, more preferably in the range from 0.1 µm to 15 µm, or much more preferably in the range from 0.3 to 2 µm. The thickness of the laminar joint 14 is preferably constant, though it may be locally increased.

In FIG. 2, the boundary surfaces between the laminar joint 14 and the materials of the first and second wires 2, 3 are clearly visible for an easier understanding. However, no such clear boundary surfaces may be present between the laminar joint 14 and the materials of the first and second wires 2, 3.

The joint 14 which is produced by welding includes therein the components (metal elements) of the metal material of the first wire 2 and the components (metal elements) of the metal material of the second wire 3. The material composition may preferably change gradually from the first wire 2 through the joint 14 to the second wire 3. The material composition may preferably change continuously from the first wire 2 through the joint 14 to the second wire 3. The joint 14 may have a portion in which at least one of the components of the material of the first wire 2 is reduced in content or concentration toward the proximal end, i.e., the second wire 3. The joint 14 may have a portion in which at least one of the components of the material of the second wire 3 is reduced in content or concentration toward the distal end, i.e., the first wire 2. More preferably, in the joint 14, at least one of the components of the material of the first wire 2 is reduced in content or concentration toward the proximal end, i.e., the second wire 3, and at least one of the components of the material of the second wire 3 is reduced toward the distal end, i.e., the first wire 2.

Specific examples will be described below. If the first wire 2 is made of an Ni—Ti base alloy and the second wire 3 is made of stainless steel (Fe—Cr—Ni base alloy), then in the joint 14, Fe and Cr have a decreasing tendency from the second wire 3 toward the first wire 2, and Ni and Ti have a decreasing tendency from the first wire 2 toward the second wire 3.

Figure 3:
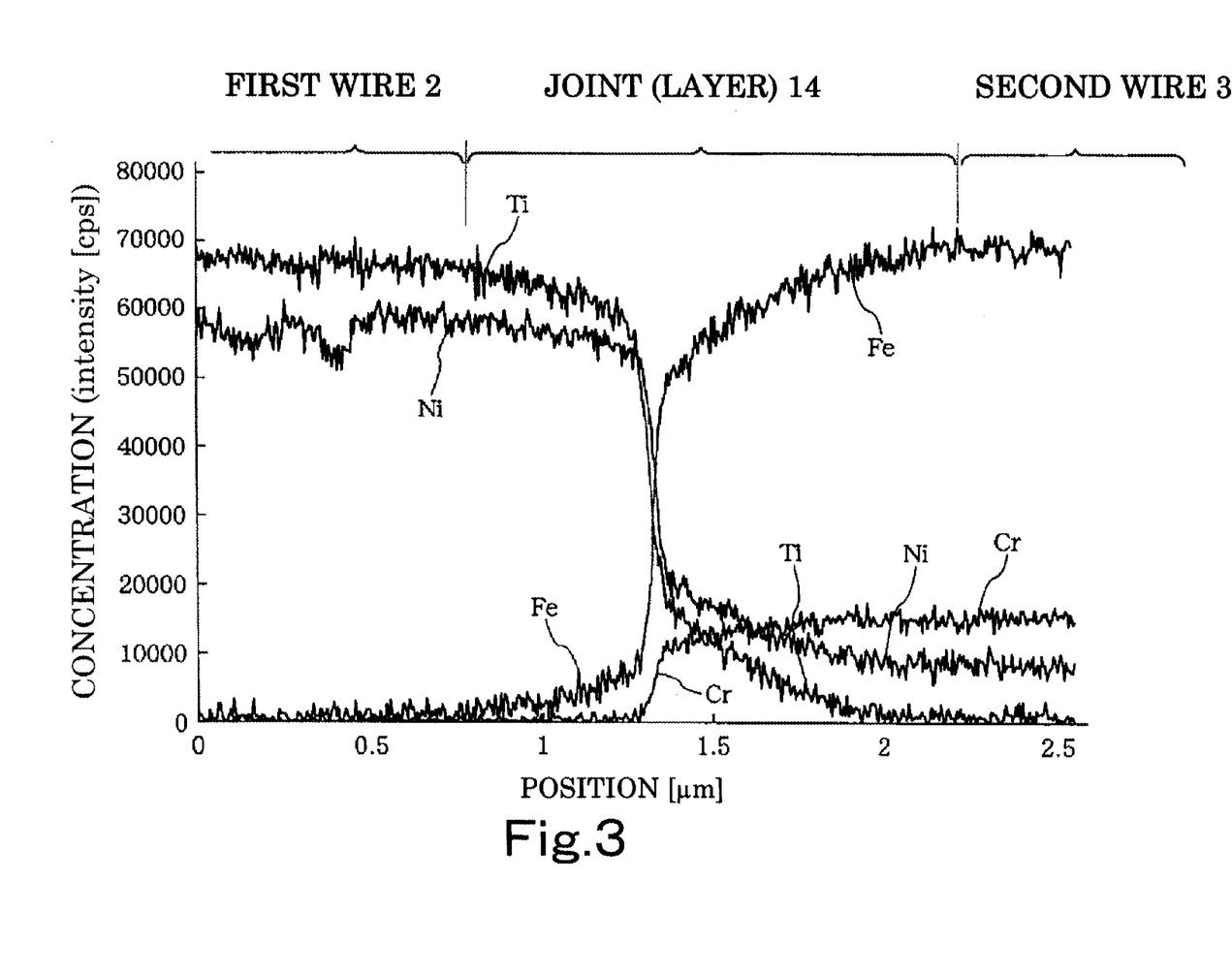
FIG. 3 is a graph showing the results of an Auger electron spectroscopic analysis of the longitudinal composition of the wire body of the guide wire shown in FIG. 1.

FIG. 3 is a graph showing the results of an Auger electron spectroscopic analysis of the composition along the longitudinal axis of a wire body which was constructed by welding, according to butt resistance welding, a first wire 2 made of Ni—Ti alloy containing 55.91 wt % of Ni and the balance being Ti and inevitable impurities including C, O, etc., and a second wire 3 made of a stainless steel (SUS302) containing 18.19 wt % of Cr, 8.03 wt % of Ni, and the balance being Fe and inevitable impurities including Mn etc.

As shown in FIG. 3, the concentrations of Ni and Ti, which are components of the first wire 2, are substantially constant in the first wire 2 and decrease in the joint 14 toward the second wire 3. In the second wire 3, the concentration of Ni is substantially constant, and the concentration of Ti is substantially nil. In the second wire 3, the concentrations of Fe and Cr, which are components of the second wire 3, are substantially constant. In the first wire 2, the concentrations of Fe and Cr are substantially nil. In the joint 14, the concentrations of Fe and Cr increase toward the second wire 3.

As shown in FIG. 3, the weld joint 14 may have at least a portion such that at least one component of the material of the first wire 2 decreases in content or concentration toward the proximal end. The weld joint 14 may have at least a portion such that at least one component of the material of the second wire 3 decreases in content or concentration toward the distal end. For example one component of the material of the first wire 2 may be Ti, and one component of the material of the second wire 3 may be Fe.

More specifically, in the joint 14, the concentrations of Ni and Ti near the first wire 2 gradually decrease toward the second wire 3, abruptly drop across a certain region, and gradually decrease near the second wire 3. That is, in a region including the joint 14, at least one of the components of the material of the first wire 2 decreases at least two different concentration gradients toward the second wire 3. The concentrations of Ni and Ti in the joint 14 have a first concentration gradient gradually decreasing near the first wire 2 toward the proximal end, a second concentration gradient gradually decreasing near the second wire 3 toward the proximal end, and a third concentration gradient positioned intermediate between the first and second concentration gradients and steeper than the first and second concentration gradients. In the joint 14, the concentration of Fe near the second wire 3 gradually decreases toward the distal end, abruptly drops across a certain region, and gradually decreases near the first wire 2. That is, in a region including the joint 14, at least one of the components of the material of the second wire 3 decreases at least two different concentration gradients toward the first wire 2. The concentration of Fe in the joint 14 has a first concentration gradient gradually decreasing near the second wire 3 toward the distal end, a second concentration gradient gradually decreasing near the first wire 2 toward the distal end, and a third concentration gradient positioned intermediate between the first and second concentration gradients and steeper than the first and second concentration gradients.

The first and second concentration gradients and the third concentration gradient may be analyzed as follows: When the first and second wires 2, 3 are welded to each other, the components typified by Ni and Ti of the first wire 2 and Fe, Cr, and Ni of the second wire 3 are mixed with each other. When Fe and Ti are mixed with each other, they usually produce a brittle intermetallic compound. According to the present invention, the area where Fe and Ti are mixed with each other is highly thinned to make the intermetallic compound hardly brittle. The area where Fe and Ti are mixed with each other corresponds to the third concentration gradient. At the first and second concentration gradients on both sides of the third concentration gradient, the components Fe and Ti are considered to be gradually reduced or increased by way of diffusion. Since the first and second concentration gradients are present continuously on both sides of the third concentration gradient, the continuity of the atomic arrangement is maintained, and abrupt property changes are lessened, making the intermetallic compound hardly brittle. As the first and second concentration gradients, which are more gradual than the third concentration gradient, are present on both sides of the third concentration gradient, the joint 14 keeps a strong bonding strength against not only tensile stresses, but also bending and torsional stresses.

The elements may be analyzed not only by the Auger electron spectroscopic analysis, but also by any of various analyses including an X-ray photoelectron spectroscopic analysis (XPS), an electron probe X-ray microanalysis (EPMA), a fluoroscopic X-ray analysis, etc.

The change in the composition (components) in the joint 14 and wire regions on both sides thereof provide a higher bonding strength.

The first wire 2 and the second wire 3 may be welded to each other by any welding processes, e.g., friction welding, laser-beam spot welding, butt resistance welding such as butt seam welding, etc. Of these welding processes, butt resistance welding is preferable for its ability to achieve a relatively high bonding strength relatively simply. When the first wire 2 and the second wire 3 are welded to each other by butt resistance welding, the following conditions are preferable which depend upon the materials and the outside diameters of the wires to be welded. The wires may be pressurized under a pressure ranging from 30 kgf/mm$^2$ to 400 kgf/mm$^2$. If the pressure is lower than 30 kgf/mm$^2$, a spark failure will occur. If the pressure is higher than 400 kgf/mm$^2$, the welding machine will possibly be broken. More preferably, the wires may be pressurized under a pressure ranging from 50 kgf/mm$^2$ to 200 kgf/mm$^2$. The value of a current to be passed through the wires is preferably in the range from 40 A to 1000 A. If the current value is lower than 40 A, the bonding strength will be weaker, and if the current value is higher than 1000 A, the bonding strength will be relatively significantly lowered. More preferably, the value of the current may be in the range from 60 A to 700 A. The current may be passed preferably for a period of time ranging from 5 ms to 100 ms. If the period of time for which the current is passed is shorter than 5 ms, relatively no desired current value will be achieved, and if the period of time for which the current is passed is longer than 100 ms, the bonding strength will not be significantly increased. More preferably, the current may be passed for a period of time ranging from 10 ms to 60 ms.

The joint 14 may be of a planar shape, although as mentioned above, the joint 14 is preferably of a curved shape as shown in FIGS. 1 and 2. Particularly, the joint 14 may be convex toward the proximal end of the wire body 10. Alternatively, the joint 14 may be convex toward the distal end of the wire body 10. The curved shape of the joint 14 is preferably substantially symmetric with respect to the central axis of the wire body 10. Specifically, the curved shape of the joint 14 is preferably shaped as a body of rotation about the central axis of the wire body 10. The body of rotation may be of a dish shape, a spherical shape, a parabolic shape, or a shape similar to one of those shapes.

The outside diameter of the wire body 10 at the joint 14 is greater than the outside diameter of a proximal side of the joint 14. More preferably, as shown in FIG. 2, the outside diameter of the wire body 10 at the joint 14 is greater than the outside diameters of the distal and proximal sides of the joint 14. A certain region of the wire body 10, which includes the joint 14, has a portion 17 projecting (raised) radially outwardly. The portion 17 gives a greater joint area to the joint 14 for increased bonding strength, which allows torsional torques and pushing forces to be transmitted from the second wire 3 to the first wire 2.

The portion 17 also makes it possible to relatively easily visually recognize an area where the joint 14 is present according to radioscopy, for example. As a result, the manner in which the guide wire 1 or the catheter combined therewith travels through a blood vessel can be easily and reliably grasped or determined by confirming the radioscopic image, resulting in a reduction in the period of time required to operate on the patient and an increase in the safety of the guide wire 1.

The height or radial dimension of the portion 17 is preferably in the range from 1 μm to 0.4 mm, and more preferably from 5 μm to 50 μm. If the height of the portion 17 is less than the lower limit, the advantages of the portion 17 may not possibly be offered depending on the materials of the first wire 2 and the second wire 3. If the height of the portion 17 exceeds the upper limit, it may be difficult for the second wire 3 to possess the desired properties. Since the inside diameter of a lumen to be inserted into the balloon catheter is determined, the outside diameter of the second wire 3 closer to the distal end has to be reduced compared with the height of the portion 17.

By way of example, the portion 17 can be formed as follows. The proximal end of the first wire 2 and the distal end of the second wire 3 are held under pressure in contact with each other while a certain voltage is applied thereto by a butt welding machine, for example. When the first and second wires 2, 3 are held under pressure in contact with each other, a molten layer is formed in the contacting region. The molten layer is cooled and solidified to form the joint 14, firmly joining the first wire 2 and the second wire 3. When the first and second wires 2 and 3 are welded together, a raised portion having a large outside diameter is formed in a certain region including the joint 14, e.g., a region extending over 0.1 mm to 5 mm across the joint 14. The raised portion is appropriately removed (deleted) to shape and thus form the portion 17. The portion 17 may have a substantially smooth outer circumferential surface. The raised portion may be removed by grinding, polishing, or chemical processing such as etching or the like.

A tube-like member may be disposed about the region including the joint 14. The region has a smaller diameter portion. The diameter of the region is preferably the same as an inner diameter of the tube-like member. The tube-like member includes a cylindrical member, a mesh-like member and a coil-like member.

Figure 4:
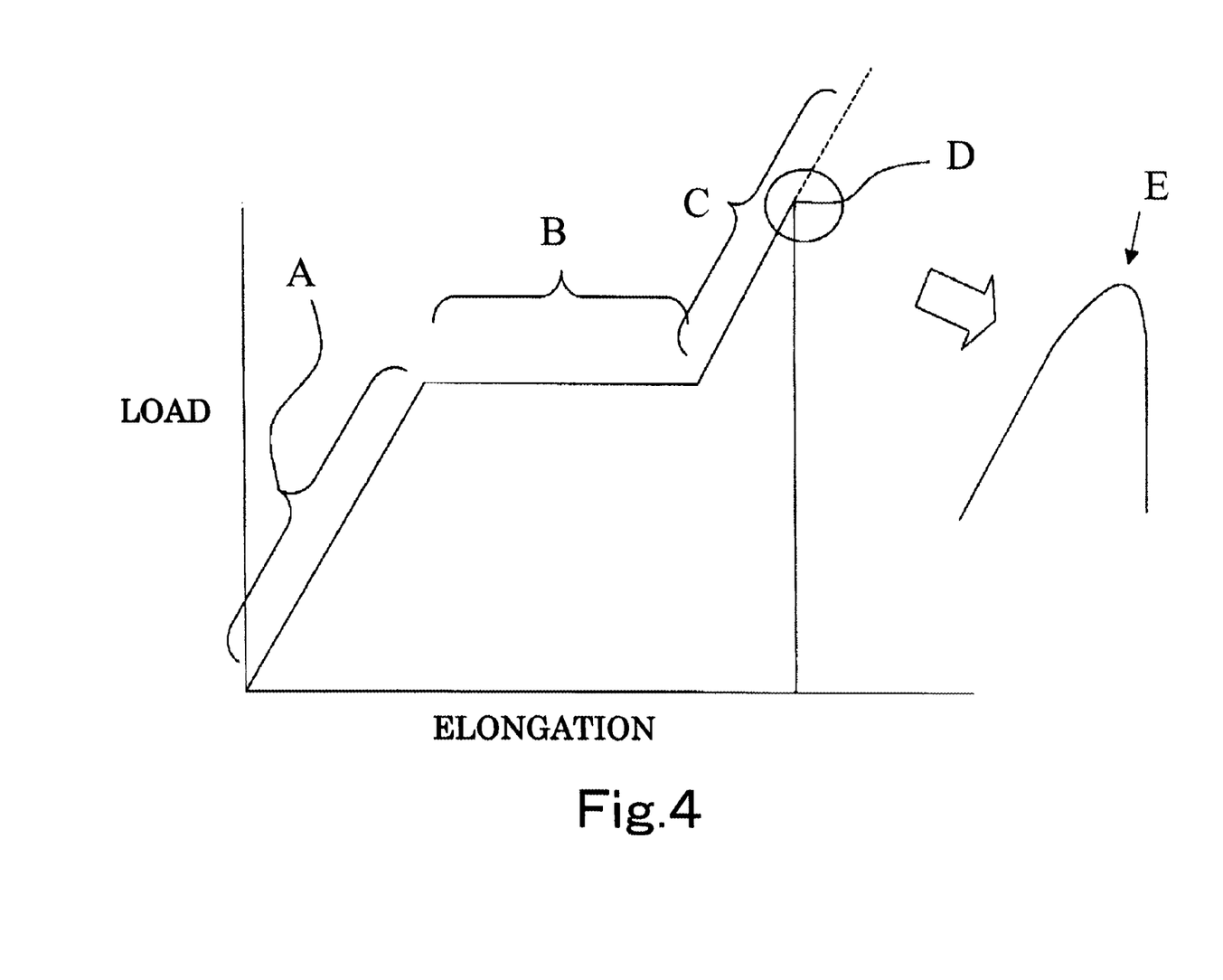
FIG. 4 is a diagram showing the relationship between tensile loads and elongations in a tensile test conducted on the wire body shown in FIG. 1.
Figure 5:
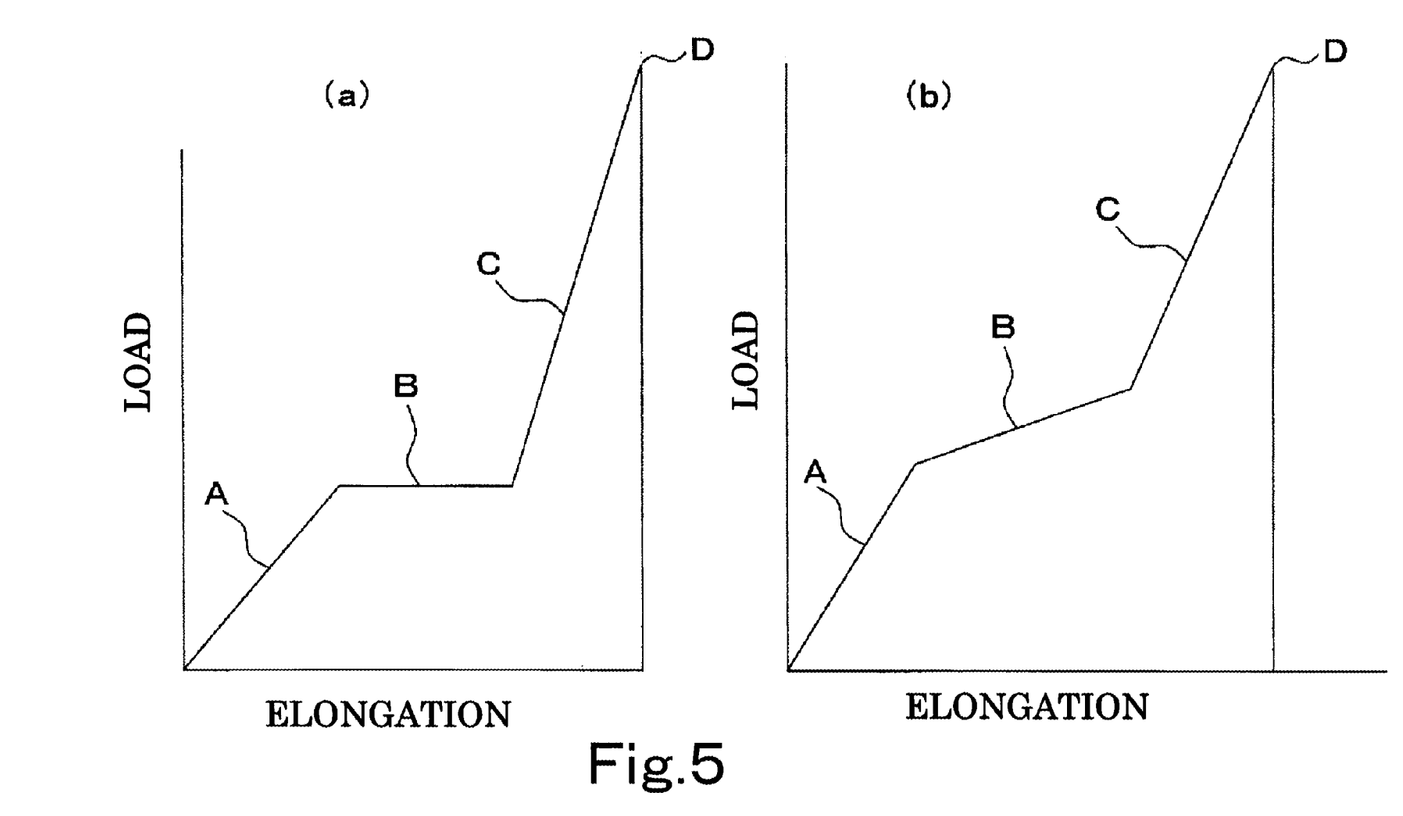

The wire body 10 has the following mechanical characteristics. FIGS. 4, 5(a), and 5(b) are diagrams showing the relationship between tensile loads and elongations in a tensile test conducted on the wire body 10. The mechanical characteristics of the wire body 10 will be described in detail below with reference to FIGS. 4, 5(a), and 5(b).

A tensile test is conducted on a region of the wire body 10. In a wire body 10 having a certain length including the joint 14, e.g., the region has a length ranging from 20 mm to 60 mm across the joint 14. The tensile load and elongation diagram shown in FIG. 4 has an elastic section A, a yield section B, and a straight section C. The elastic section A extends substantially straight upwardly to the right. The yield section B extends substantially horizontally (or upwardly to the right) from the elastic section A. The straight section C extends substantially straight upwardly to the right from the yield section B. The wire body 10 is fractured near the terminal end of the straight section C under a load higher than at the terminal end of the yield section B. The wire body 10 is fractured at a position other than the joint 14, i.e., somewhere at the first wire 2 or somewhere at the second wire 3.

When the wire body 10 starts being pulled, the substantially straight elastic section A first appears in the tensile load and elongation diagram. As more load is applied to the wire body 10 from the elastic section A, the yield section B having a less gradient than the elastic section A appears in the tensile load and elongation diagram.

Since the first wire 2 is made of a material having smaller elastic constants than the second wire 3, the elastic section A is considered to be developed by the physical properties of the material of the first wire 2. If the first wire 2 itself exhibits a substantially horizontal tensile load and elongation curve, the yield section B is represented by a substantially straight and horizontal (flat) curve (see FIG. 4). The joint 14 is not fractured at the terminal end (the right end in FIG. 4) of the yield section B. That is, the layer itself forming the joint 14 (inside the layer), the boundary between the layer and the first wire 2, and the boundary between the layer and the second wire 3 are not fractured.

Then, the substantially straight section C extending upwardly to the right appears beyond the yield section B. The straight section C is considered to be developed by the physical properties of the materials of both the first and second wires 2, 3. The joint 14 has fracture strength beyond the yield section B. Therefore, even when the first wire 2, which is more flexible than the second wire 3, is pulled, bent, or twisted closely at the joint 14 under forces corresponding to the terminal end of the yield section B, the joint 14 remains joined. Accordingly, the guide wire 1 is highly reliable and safe.

As more load is applied to the wire body 10, the wire body 10 is eventually fractured at a fracture point D in the straight section C. The fracture is represented by a curve extending vertically downwardly from the fracture point D in the tensile load and elongation diagram of FIG. 4. The terminal end of the straight section C is the fracture point D. An inspection of the fracture point D at an enlarged scale indicates that the tensile load and elongation curve has a curved section E where the tensile load and elongation curve reaches a peak and then falls downwardly (see an enlarged area in FIG. 4).

The curved section E appears when the distal end of the second wire 3 causes necking (a constriction due to a reduction in the outside diameter, also referred to as neck-down) as the wire body 10 approaches the fracture point D. As the degree of necking is smaller, the radius of curvature of the curved section E is smaller, resulting in a sharper peak. Such necking means that the wire material is tougher, preventing the guide wire from causing abrupt fracture even when subjected to excessive stresses.

The wire body 10 is often fractured generally at the position where it has suffered necking. The fact that the distal end of the second wire 3, where necking has occurred, is fractured means that the layer itself of the joint 14 (inside the layer), the boundary between the layer and the first wire 2, and the boundary between the layer and the second wire 3 are not fractured, and that the joint 14 has a higher fracture strength than the distal end of the second wire 3. As a result, the guide wire 1 is highly reliable and safe.

The fracture strength of the wire body 10 is preferably 4 kgf or higher, or more preferably 5 kgf or higher, or much more preferably 8 kgf or higher.

FIGS. 5(a) and 5(b) show other patterns of tensile load and elongation diagrams. According to the tensile load and elongation diagram shown in FIG. 5(a), the elastic section A and the yield section B are essentially the same as those shown in FIG. 4, but the straight section C has a greater gradient (rises more steeply) than the straight section C shown in FIG. 4. Such a tendency appears if the second wire 3 is made of a material having greater elastic constants (higher rigidity) or the second wire 3 has a greater outside diameter.

According to the tensile load and elongation diagram shown in FIG. 5(b), the elastic section A and the straight section C are essentially the same as those shown in FIG. 4, but the yield section B extends upwardly to the right and is substantially straight. The gradient of the yield section B is smaller than the gradient of the elastic section A and smaller than the gradient of the straight section C. For example, this tendency is exhibited if the first wire 2 itself is made of a pseudoelastic material represented by a tensile load and elongation curve (stress and strain curve) that extends upwardly to the right even after the yield point. The tendency is also exhibited if the first wire 2 is of a tapered shape having an outside diameter progressively reduced in the vicinity of the joint 14 toward the distal end. In addition, a load beyond the elastic section A is applied to the tapered portion of the first wire 2. Even if the first wire 2 is made of a material exhibiting a flat yield section, the shape of the first wire 2 affects the tensile load and elongation curve to cause the yield section B to have a gradient.

If the tensile rate in a tensile test on the wire body 10 is relatively low, e.g., if the tensile rate is about 0.5 mm/min., the yield section B of the tensile load and elongation curve tends to be horizontal or extend upwardly to the right at a relatively small gradient. If the tensile rate is relatively high, e.g., if the tensile rate is about 5 mm/min., then the yield section B of the tensile load and elongation curve tends to extend upwardly to the right at a relatively large gradient.

Figure 6:
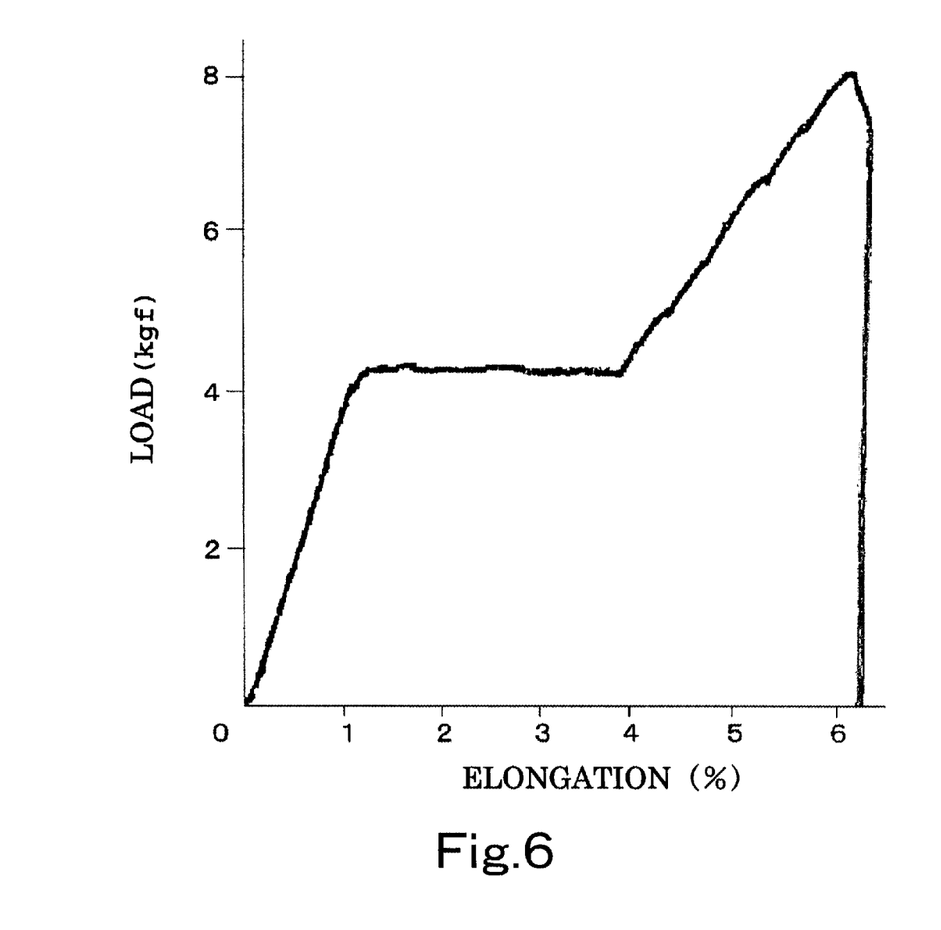
FIG. 6 is a diagram showing the relationship between tensile loads and elongations in a tensile test conducted on the wire body shown in FIG. 1.

A specific example will be described below. The tensile test is conducted as follows on a region of the wire body 10 including the joint 14 according to the present invention. An Ni—Ti alloy wire having an outside diameter of 0.335 mm (first wire 2) and a stainless steel (SUS302) wire having an outside diameter of 0.335 mm (second wire 3) were welded to each other by butt resistance welding. Further, a raised portion (burr) formed on the joint was mechanically polished off to provide a substantially uniform outside diameter. The test specimen thus formed was fixed to the chucks of a tensile tester such that the Ni—Ti alloy wire was positioned upwardly, the stainless steel wire was positioned downwardly, and the joint was positioned centrally. The distance between the chucks was 40 mm, and the length of each of the Ni—Ti alloy wire and the stainless steel wire was 20 mm. The tensile rate was 0.5 mm/min. Under the above conditions, the test specimen was pulled until it was fractured. FIG. 6 shows a tensile load and elongation diagram of the tensile test.

In FIG. 6, a region of the joint 14 of the test specimen exhibits a substantially straight elastic section extending upwardly to the right. As more load is applied to the test specimen, a substantially horizontal yield section was developed under a load in excess of 4 kg. Then, a straight section extending upwardly to the right appeared. The test specimen caused necking when it was elongated 6% under a load of 8 kgf, after which the test specimen was fractured. Actually, the test specimen was fractured at a position on the stainless steel wire near the joint 14, but not at the joint 14. This indicates that the joint 14 has higher fracture strength than the distal end of the second wire 3 in the guide wire of the present invention.

The tensile load and elongation diagrams shown in FIGS. 4 and 5(a), 5(b) are schematically illustrated only. The present invention covers various changes or modifications in those tensile load and elongation diagrams, such as slight curves in straight sections and round curves in bent sections. Thus, the tensile load and elongation curves according to the present invention are not limited to the specific patterns illustrated in FIGS. 4, 5(a), and 5(b).

As shown in FIG. 1, the wire body 10 also has the covering layer 5 covering all or part of the outer circumferential surface (outer surface) thereof. It is to be noted that the covering layer 5 is omitted from the illustration in FIG. 2. The covering layer 5 may be formed for various purposes. According to one purpose, the covering layer 5 serves to reduce friction (sliding resistance) and improve the slidability of the guide wire 1 for increased steerability of the guide wire.

The covering layer 5 is preferably provided in covering relation to the outer circumference of at least the joint 14. As described above, since the outside diameter of the wire body 10 has a change (a step) in the vicinity of the joint 14, the covering layer 5 cancels or reduces this outside diameter change, making the outside diameter of the guide wire 1 substantially uniform in the vicinity of the joint 14. As a result, the steerability of the guide wire 1 for longitudinal movement thereof is improved.

To serve the above purpose, the covering layer 5 is preferably made of a material capable of reducing friction. If the covering layer 5 is made of such a material, the frictional resistance (sliding resistance) thereof with respect to the inner wall of the catheter used in combination with the guide wire 1 is reduced for increased slidability, thus improving the steerability of the guide wire 1 in the catheter. Since the sliding resistance of the guide wire 1 is lowered, when the guide wire 1 is moved and/or rotated in the catheter, the guide wire 1 is more reliably prevented from kinking or twisting especially in the vicinity of the joint 14.

Materials capable of reducing friction include, for example, polyolefin such as polyethylene or polypropylene, polyvinyl chloride, polyester (PET, PBT, etc.), polyamide, polyimide, polyurethane, polystyrene, polycarbonate, silicone resin, fluorine-based resin (PTFE, ETFE, etc.), and their composite materials.

Of the above materials, fluorine-based resin or its composite material is capable of more effectively reducing frictional resistance (sliding resistance) between the guide wire 1 and the inner wall of the catheter for increased slidability and improved steerability of the guide wire 1 in the catheter. When the guide wire 1 is moved and/or rotated in the catheter, the guide wire 1 is reliably prevented from kinking or twisting especially in the vicinity of the joint 14.

If fluorine-based resin or its composite material is used, then it is heated and applied as the covering layer 5 to the wire body 10 usually by baking or spraying. The wire body 10 and the covering layer 5 thus applied thereto adhere closely to each other.

If silicone resin or its composite material is used, then it can be applied as the covering layer 5 to the wire body 10 without being heated. The covering layer 5 thus formed is reliably and firmly held in close adhesion to the wire body 10. Specifically, if the covering layer 5 is made of silicone resin or its composite material, the material may be a reaction-curable material. The covering layer 5 may be formed at room temperature. With the covering layer 5 formed at room temperature, the wire body 10 can easily be coated with the covering layer 5. Further, the guide wire 3 can be steered while the bonding strength of the joint 14 between the first wire 2 and the second wire 3 is being kept at a sufficient level.

Other preferable materials capable of reducing friction may be hydrophilic materials and hydrophobic materials. Of these materials, hydrophilic materials are preferable.

Hydrophilic materials include cellulose-based high-polymer materials, polyethylene-oxide-based high-polymer materials, maleic-anhydride-based high-polymer materials (e.g., maleic anhydride copolymer such as methyl vinyl ether-maleic anhydride copolymer), acrylamide-based high-polymer materials (e.g., polyacrylamide, polyglycidyl methacrylate-dimethylacrylamide (PGMA-DMAA) block copolymer), water-soluble nylon, polyvinyl alcohol, polyvinyl pyrrolidone, etc.

These hydrophilic materials exhibit a lubricating capability when wetted (absorbing water) and reduce the frictional resistance (sliding resistance) between the guide wire 1 and the inner wall of the catheter that is used in combination therewith. The slidability of the guide wire 1 is thus increased to improve the steerability of the guide wire 1 in the catheter.

The covering layer 5 may be provided for purposes of increasing safety at the time the guide wire 1 is inserted into a blood vessel. To serve this purpose, the covering layer 5 is preferably made of a flexible material (soft material).

Flexible materials that can be used include, for example, polyolefin such as polyethylene or polypropylene, polyvinyl chloride, polyester (PET, PBT, etc.), polyamide, polyimide, polyurethane, polystyrene, silicone resin, thermoplastic elastomer such as polyurethane elastomer, polyester elastomer, polyamide elastomer, or the like, various rubber materials including latex rubber, silicone rubber, etc., or composite materials in the form of a combination of two or more of the above materials.

If the covering layer 5 is made of thermoplastic elastomer such as polyurethane elastomer or the like or any of the rubber materials, since the distal end of the guide wire 1 is made more flexible, it reliably prevents damage to the blood vessel wall when inserted into a blood vessel, and is highly safe in use.

The covering layer 5 may include a laminated assembly of two or more layers, and may have different material compositions depending on the location on the wire body 10. For example, the covering layer 5 may be made of one material in a region covering the joint 14 and a different material in another region. The covering layer 5 on the distal end of the guide wire 1, e.g., the region closer to the distal end than the tapered portion 16, may be made of a soft material, as described above, for increased safety, and the covering layer 5 on the other region may be made of a friction-reducing material, as described above, for increased steerability.

The thickness of the covering layer 5 is not limited, and may be selected in view of the purpose and the material of the covering layer 5, and the method by which the covering layer 5 is formed. Usually, the thickness (average thickness) of the covering layer 5 is preferably in the range from 1 μm to 30 μm, and more preferably from 2 μm to 15 μm. If the covering layer 5 is too thin, the purpose of the covering layer 5 may not sufficiently be met, and the covering layer 5 may possibly be peeled off. If the covering layer 5 is too thick, the covering layer may possibly adversely affect the physical properties of the wire body 10, and the covering layer 5 may possibly be peeled off.

According to the present invention, the outer circumferential surface of the wire body 10 may be treated by way of chemical treatment, heat treatment, or the like for increasing the adhesion of the covering layer 5 to the wire body 10. Alternatively, an intermediate layer capable of increasing the adhesion of the covering layer 5 may be provided on the outer circumferential surface of the wire body 10.

Figure 7:
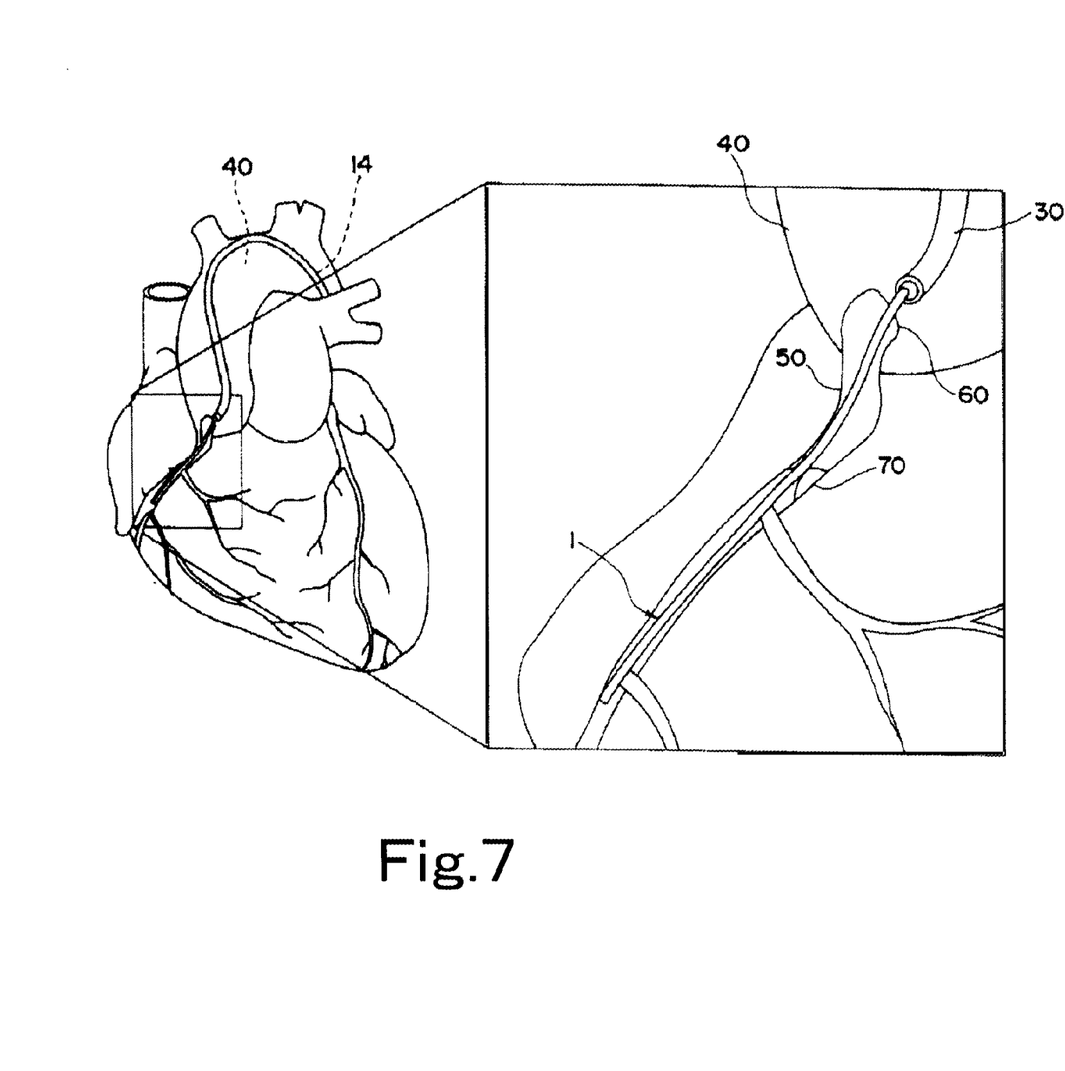
FIG. 7 is a view illustrative of an example in which the guide wire shown in FIG. 1 is used.
Figure 8:
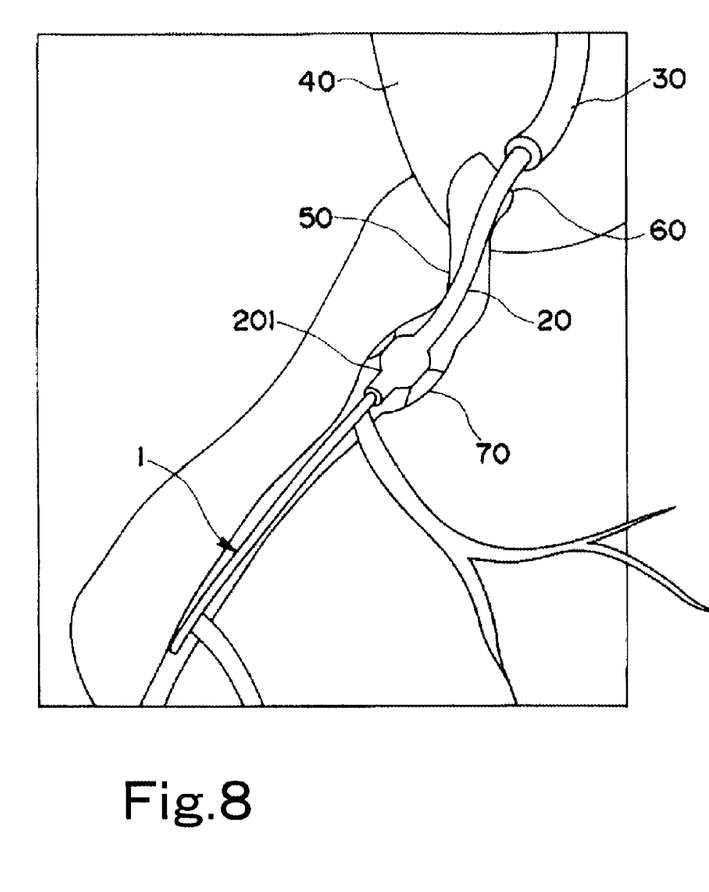
FIG. 8 is an enlarged view illustrative of the example in which the guide wire shown in FIG. 1 is used.

FIGS. 7 and 8 illustrate an example in which the guide wire 1 according to the present invention is used in PTCA. FIGS. 7 and 8 show an aortic arch 40, a right coronary artery 50, a right coronary artery opening 60, and a blood vessel constriction (lesion) 70. A guiding catheter 30 serves to guide the guide wire 1 from a femoral artery reliably into the right coronary artery 50. A balloon catheter 20 for dilating the blood vessel constriction 70 has a dilatable/contractible balloon 201 on its distal end portion as shown in FIG. 8. The following operation is performed according to radioscopy.

As shown in FIG. 7, the distal end of the guide wire 1 is projected from the distal end of the guiding catheter 30, and inserted from the right coronary artery opening 60 into the right coronary artery 50. The guide wire 1 is further moved on in the right coronary artery 50 and then stopped when the distal end of the guide wire 1 reaches a position beyond the blood vessel constriction 70. A passage for the balloon catheter 20 is now formed. At this time, the joint 14 of the guide wire 1 is positioned in a descending aorta of the aortic arch 40.

Then, as shown in FIG. 8, the distal end of the balloon catheter 20, which is inserted from the proximal end of the guide wire 1, is projected from the guiding catheter 30, and is further moved along the guide wire 1 so as to be inserted from the right coronary artery opening 60 into the right coronary artery 50. The distal end of the balloon catheter 20 is then stopped when the balloon 201 reaches the blood vessel constriction 70.

A balloon-dilating fluid is then poured into the balloon catheter 20 from the distal end thereof to dilate the balloon 201, thereby dilating the blood vessel constriction 70. A deposit such as of cholesterol on the blood vessel wall in the blood vessel constriction 70 is physically dilated, thereby eliminating the blood flow blockage.

The guide wire according to the present invention has been described above with respect to the illustrated embodiment. However, the present invention is not limited to the details and features of the illustrated embodiment. The components of the guide wire according to the present invention may be replaced with other components or members that are capable of the same functions, and other components or members may be added to the guide wire.

In addition, the guide wire according to the present invention is not limited to the use in PTCA.

The principles of the present invention have been described as being applied to a guide wire. However, the principles of the present invention are also applicable to uses than a guide wire, e.g., an interventional device such as a catheter having a component made up of a distal end member and a proximal end member that are welded to each other. Other interventional devices include, by way of example and not limitation, baskets, and retrieval devices.

Although certain preferred embodiments of the present invention has been shown and described in detail, it should be understood that various changes and modifications may be made therein without departing from the scope of the appended claims.

What is claimed is:

1. A method of making an interventional device comprising:
   providing a first member having a proximal end portion;
   providing a second member having a distal end portion and being made of a material having an elastic constant greater than an elastic constant of the material of which said first member is made;
   butt resistance welding said proximal end portion of said first member and said distal end portion of said second member; and
   said butt resistance welding comprising pressuring said proximal end portion of said first member and said distal end portion of said second member under a pressure ranging from 30 kgf/mm2 to 400 kgf/mm2.

2. The method of making an interventional device according to claim 1:
   said butt resistance welding comprising passing a current through said members in the range from 40 A to 1000 A.

3. The method of making an interventional device according to claim 1:
   said butt resistance welding comprising passing current for a period of time ranging from 5 ms to 100 ms.

4. The method of making an interventional device according to claim 1:
   said interventional device is a guide wire.

5. The method of making an interventional device according to claim 1:
   said interventional device is one of a catheter, a basket, and a retrieval device.

6. A method of making an interventional device comprising:
   providing a first member having a proximal end portion;
   providing a second member having a distal end portion and being made of a material having an elastic constant greater than an elastic constant of the material of which said first member is made;
   wherein the proximal end portion of the first member has one of a convex or a concave shape and the distal end portion of the second member has a complimentary convex or a complimentary concave shape relative to the proximal end portion of the first member;
   friction welding said proximal end portion of said first member and said distal end portion of said second member to produce a member body having a central axis in which a joining surface between the proximal end portion of said first member and the distal end portion of said second member forms a joint having a curved shape defined by the complimentary convex and concave shapes of the first and second members, the entire curved shape of the joint being symmetrical with respect to said central axis of said member body.

7. The method of making an interventional device according to claim 6:
   said interventional device is a guide wire.

8. The method of making an interventional device according to claim 6:
   said interventional device is one of a catheter, a basket, and a retrieval device.

9. The method of making an interventional device according to claim 6:
   wherein the curved shape of the joint between said first member and said second member is convex.

10. The method of making an interventional device according to claim 6:
   wherein the curved shape of the joint between said first member and said second member defines a body of rotation about said central axis of said member body.

* * * * *